United States Patent
Bogatu et al.

(10) Patent No.: US 12,178,553 B2
(45) Date of Patent: Dec. 31, 2024

(54) CONTROL UNIT FOR DERIVING A MEASURE OF ARTERIAL COMPLIANCE

(71) Applicant: KONINKLIJKE PHILIPS N.V., Eindhoven (NL)

(72) Inventors: Laura Ioana Bogatu, Eindhoven (NL); Jens Muehlsteff, Aachen (DE); Maarten Petrus Joseph Kuenen, Veldhoven (NL); Erik Bresch, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 818 days.

(21) Appl. No.: 17/416,220

(22) PCT Filed: Dec. 9, 2019

(86) PCT No.: PCT/EP2019/084118
§ 371 (c)(1),
(2) Date: Jun. 18, 2021

(87) PCT Pub. No.: WO2020/126576
PCT Pub. Date: Jun. 25, 2020

(65) Prior Publication Data
US 2022/0071496 A1    Mar. 10, 2022

(30) Foreign Application Priority Data
Dec. 18, 2018   (EP) .................................. 18213276

(51) Int. Cl.
*A61B 5/02* (2006.01)
*A61B 5/021* (2006.01)
(Continued)

(52) U.S. Cl.
CPC ...... *A61B 5/02007* (2013.01); *A61B 5/02125* (2013.01); *A61B 5/02225* (2013.01);
(Continued)

(58) Field of Classification Search
CPC . A61B 5/02007; A61B 5/021; A61B 5/02108; A61B 5/02116; A61B 5/02125;
(Continued)

(56) References Cited

U.S. PATENT DOCUMENTS

| | | |
|---|---|---|
| 3,920,004 A | 11/1975 | Nakayama |
| 5,711,303 A | 1/1998 | Shimizu et al. |

(Continued)

FOREIGN PATENT DOCUMENTS

| | | |
|---|---|---|
| WO | 1995007650 A1 | 3/1995 |
| WO | 2017216268 A1 | 12/2017 |

OTHER PUBLICATIONS

International Search Report and Written Opinion, International Application No. PCT/EP2019/084118, Mailed on Feb. 11, 2020.
(Continued)

*Primary Examiner* — Eric F Winakur
*Assistant Examiner* — Abel Seifu Abegaz (57) ABSTRACT

The invention provides a controller and method for deriving a measure of arterial compliance based on an acquired arterial volume variation signal and an acquired pulse arrival time signal. An oscillometric blood pressure measurement device is used to acquire the arterial volume variation signal. Arterial volume and variation in pulse arrival time are both measured as an applied pressure to an artery are varied by the oscillometric blood pressure measurement device. The arterial volume signal is transformed into a corresponding signal representative of variation in peak-to-peak amplitude of the arterial volume.

15 Claims, 3 Drawing Sheets

(51) Int. Cl.
  *A61B 5/022*   (2006.01)
  *A61B 5/0225*  (2006.01)
  *A61B 5/024*   (2006.01)
  *A61B 5/318*   (2021.01)

(52) U.S. Cl.
  CPC ........ *A61B 5/0225* (2013.01); *A61B 5/02416* (2013.01); *A61B 5/318* (2021.01)

(58) Field of Classification Search
  CPC ..... A61B 5/022; A61B 5/024; A61B 5/02416; A61B 5/0245
  See application file for complete search history.

(56) References Cited

U.S. PATENT DOCUMENTS

| | | |
|---|---|---|
| 2003/0167012 A1 | 9/2003 | Friedman et al. |
| 2006/0247538 A1 | 11/2006 | Davis |
| 2012/0197142 A1* | 8/2012 | Lovejoy ............... A61B 5/4848 600/507 |
| 2013/0023777 A1 | 1/2013 | Tokko et al. |
| 2017/0079533 A1* | 3/2017 | Robinson ........... A61B 5/02116 |
| 2017/0354331 A1 | 12/2017 | Borkholder et al. |

OTHER PUBLICATIONS

Zheng, D. et al., "Peripheral arterial volume distensibility: significant differences with age and blood pressure measured using an applied external pressure; peripheral arterial volume distensibility", Physiological Measurement, Institute of Physics Publishing, vol. 32, No. 5, Mar. 2011.

Wilkinson IB, Webb DJ. Venous occlusion plethysmography in cardiovascular research: methodology and clinical applications. Br. J. Clin. Pharmacol. 2001;52:631-646. doi: 10.1046/j.0306-5251.2001.01495.x.

Ras, R. T., Streppel, M. T., Draijer, R. & Zock, P. L. Flow-mediated dilation and cardiovascular risk prediction: a systematic review with meta-analysis. Int J Cardiol 168, 344-351.

Selvaraj N, et al. Influence of respiratory rate on the variability of blood volume pulse characteristics. J Med Eng Technol. 2009;33(5):370-375. doi: 10.1080/03091900802454483.

Wu HT, Lin BY, Yang CC, Ou YN, Sun CK, Assessment of Vascular Health With Photoplethysmographic Waveforms From the Fingertip. IEEE J Biomed Health Inform. Mar. 2017;21(2):382-386. doi: 10.1109/JBHI.2016.2515938.

Zahedi E, Jaafar R, Ali MAM, Mohamed AL, Maskon O. Finger photoplethysmogram pulse amplitude changes induced by flow-mediated dilation. Physiol Meas. 2008;29:625-37.

Maas JJ, Pinsky MR, Geerts BF, de Wilde RB, Jansen JR. Estimation of mean systemic filling pressure in postoperative cardiac surgery patients with three methods. Intensive Care Med. 2012;38:1452-1460. doi: 10.1007/s00134-012-2586-0.

Aya HD, Rhodes A, Fletcher N, Grounds RM, Cecconi M. Transient stop-flow arm arterial-venous equilibrium pressure measurement: determination of precision of the technique. J Clin Monit Comput. 2016;30(1):55-61. doi: 10.1007/s10877-015-9682-y.

Seagar, A.D., Gibbs, J.M. & Davis, F.M. Med. Biol. Eng. Comput. (1984) 22: 12. https://doi.org/10.1007/BF02443739.

Drzewiecki G et al (1994). Theory of the oscillometric maximum and the systolic and diastolic detection ratios. Annals of Biomedical Engineering, 22, pp. 88-96.

Bresch E., Muehlsteff J., Schmitt L. (2018) Cuff-induced changes of pulse arrival time: models and experimental results. In: Eskola H., Väisänen O., Viik J., Hyttinen J. (eds) EMBEC & NBC 2017. EMBEC 2017, NBC 2017. IFMBE Proceedings, vol. 65. Springer, Singapore.

* cited by examiner

CONTROL UNIT FOR DERIVING A MEASURE OF ARTERIAL COMPLIANCE

This application is the U.S. National Phase application under 35 U.S.C. § 371 of International Application No. PCT/EP2019/084118, filed on 9 Dec. 2019, which claims the benefit of European Application Serial No. 18213276.1, filed 18 Dec. 2018. These applications are hereby incorporated by reference herein.

FIELD OF THE INVENTION

This invention relates to a control unit and method, for deriving a measure of arterial compliance.

BACKGROUND OF THE INVENTION

When monitoring a patient's condition in a clinical setting, early detection of critical states of the patient is important. Common monitored parameters of a patient such as heart rate or blood pressure lack specificity in indicating particular condition or problem, and are often encumbered by a time lag between patient deterioration and change in the parameter. For example, a hypotension phase may only become apparent from a blood pressure signal after the phase has been entered, thus precluding any preventative action. One valuable source of clinical information, which is currently under-explored, is that of arterial (or vascular) compliance. This is indicative of various parameters related to circulatory integrity. Variations in this parameter are linked to changes in blood pressure, circadian rhythms, physical activity, stress, as well as other longer-term changes caused for instance by age or lifestyle. Arterial compliance can hence reveal a large amount of information regarding health status.

Arterial compliance corresponds to the ability of arteries (specifically artery walls) to distend and contract in response to changes in arterial pressure (i.e. pressure exerted on the artery wall by flowing blood). Arterial compliance can be defined by the expression $$C_{art}(P_{tm}(t)) = \frac{dV_{art}(t)}{dP_{art}(t)} \quad (1)$$

where $V_{art}$ is arterial volume, t is time, $P_{art}$ is arterial blood pressure and $P_{tm}$ is transmural pressure (i.e. the net pressure across the artery wall). Transmural pressure, $P_{tm}$ is defined as the arterial blood pressure, $P_{art}$, minus any applied pressure being from the outside onto the artery wall, i.e. artery internal pressure minus externally applied pressure.

Arterial blood pressure $P_{art}$ oscillates with each heart cycle, with the maximum or peak value of $P_{art}$ each cycle corresponding to systolic blood pressure (SBP) and the minimum value of $P_{art}$ each cycle corresponding to diastolic blood pressure (DBP). The SBP value is the blood pressure value at the end systole phase of the heart cycle. The DBP value is the blood pressure value at the end diastole phase of the heart cycle.

Arterial compliance is affected by many different factors, and is highly person specific. It is a function in part of the transmural pressure across the artery wall ($P_{tm}$). Hence it has different values depending on the net pressure across the artery wall.

Due to its dependency on multiple physiological factors, monitoring of arterial compliance has a large number of possible applications for detecting patient deterioration.

One straightforward approach is to simply monitor changes in the arterial compliance function, and for instance present these on a display for analysis by a clinician.

Another approach is to incorporate arterial compliance information into one or more physiological models (such as that describing the Windkessel effect), for the purpose of approximating further parameters such as cardiac output or peripheral resistance (the resistance of arteries to blood flow).

In further examples, knowledge of arterial compliance can be used as a convenient (non-invasive) surrogate for blood pressure estimation.

A further example application is the use of compliance information for assessment of endothelial function (the ability of the arteries to adjust lumen size to maintain homeostasis). Usually this would be performed by means of measuring artery dimensions following an induced vascular occlusion of several minutes (flow-mediated dilation). The short term changes in blood flow produce changes in arterial lumen size, revealing information about stability of a patient (such as presence of sepsis), or progression of cardiovascular diseases. Ultrasound, photoplethysmography (PPG) or pulse arrival time (PAT) based techniques are currently employed to assess the artery dimensions.

These current techniques suffer deficiencies related to the difficulty in imaging arteries (in the case of ultrasound), and/or inconvenience for the patient, due to the fact that occlusion needs to take place for several minutes to produce a detectable change in artery size. This is uncomfortable for a patient.

Monitoring compliance may allow for more long term or ongoing assessment of endothelial response, by enabling more accurate and comfortable measurements of changes in artery size compared to current practices. In particular, duration of induced occlusion of the artery can be shortened while still achieving sufficient change in artery size for measurement of endothelial response. This allows for monitoring of endothelial response over a longer or ongoing period without causing significant discomfort for the patient.

A further example application of arterial compliance information is assessment of fluid responsiveness. Arterial compliance allows for calculating of mean systemic filling pressure for example. Mean systemic filling pressure can be derived by measurement of stop-flow forearm arterial and venous equilibrium pressures. These pressure values are input to a Guytonian model. This model allows for inferring of the mean systemic filling pressure and also the effective intravascular volume status, which contributes to the assessment of fluid responsiveness. Information about compliance permits improvement in the accuracy of the parameters used in such a model, thus leading to a better quantification of fluid responsiveness.

In a similar approach, measurement of arterial compliance could also be incorporated into assessment in limb blood flow, measured by means of venous occlusion plethysmography. This measurement is also based on employing a model which describes the physiology of the occluded limb. Accurate estimation of the model's parameters (e.g. compliance) can assist in interpreting changes in limb volume during this measurement (e.g. detection of venous thrombosis).

Hence there are many useful applications for arterial compliance.

In principle compliance can be measured by means of high resolution imaging (e.g. ultrasound), which can reveal changes in arterial diameter as arterial pressure varies between systolic and diastolic values. However, this is highly resource intensive, as it requires highly skilled operators to perform the ultrasound scan. It is also prone to errors from potential misinterpretation of the images. It also does not allow for continuous or long-term monitoring of arterial compliance, as a single scan can naturally only be representative of compliance at one point in time.

Furthermore, if information about compliance is required over a wider range of transmural pressures, then imaging technologies would need to be calibrated with steps for applying external pressure to arteries, further complicating the measurement.

An alternative approach to ultrasound imaging is to use the (typically) already available physiological signals used in clinics for patient monitoring, e.g. electrocardiogram (ECG), PPG and/or a sphygmomanometer (blood pressure measurement cuff). These signals can give information about changes in arterial volume and pressure, enabling calculation of compliance. These approaches thus allow for more practical continuous monitoring of compliance.

A sphygmomanometer is a form of blood pressure monitoring device. It comprises an inflatable cuff with an internal inflation chamber. The cuff is wrapped around a patient's arm and by inflation of the cuff, pressure is applied to the brachial artery beneath the cuff. By monitoring pressures exerted on the cuff by the artery beneath it as the applied pressure is varied, an accurate measure of arterial blood pressure can be derived.

One form of blood pressure monitoring device is an oscillometric blood pressure measurement device. This is based on detecting oscillations (i.e. oscillometric pressure signals) in the artery wall as an applied pressure is varied. These manifest in oscillations in transmural pressure across the artery wall. The amplitudes of these oscillatory signals can be used to derive an indication of systolic and diastolic blood pressure. These oscillations are measured across a range or spectrum of different externally applied pressures. Where the device comprises an inflatable cuff, this can be achieved by gradually inflating the inflatable cuff. Another form of pressure application means however can alternatively be used. The pressure variation rate is small compared to the rate of the blood pressure oscillations. Hence over small time scales, the change in detected transmural pressure can be assumed equal to the change in arterial pressure. In this way, arterial pressure oscillations can be derived.

Where the device comprises an inflatable cuff for instance, measurement of the oscillations in transmural pressure may be by means of an internal air pressure sensor in the cuff which measures oscillations in the internal inflation chamber pressure. These are indicative of the oscillating pressure applied to the cuff by the oscillating wall of the artery. It also known to derive measures of arterial volume variation using blood pressure signals obtained from oscillometric blood pressure measurement devices. Prior knowledge for instance of the elasticity of the skin contacting part of the measurement device (e.g. the inflatable cuff, where this is used) allows detected pressure changes to be processed to derive the corresponding spatial displacement, and thus the corresponding arterial volume changes.

However, currently known approaches to measuring arterial compliance via secondary monitored parameters, such as oscillometric blood pressure measurements, lack accuracy. This is because the measured signals are susceptible to sources of noise which compound when the original signal is subsequently processed to derive compliance. This distorts the final derived compliance measure.

An improved approach to measurement of arterial compliance is generally required which can both enable more long-term or ongoing monitoring and also improve accuracy of measured results compared to known approaches.

SUMMARY OF THE INVENTION

The invention is defined by the claims.

According to examples in accordance with an aspect of the invention, there is provided a control unit for deriving a measure of arterial compliance, operably coupleable in use with an oscillometric blood pressure measurement device, and a means for measuring pulse arrival time, the control unit adapted to:
acquire using the oscillometric measurement device a signal indicative of variation in arterial volume of an artery assumed to be in contact with the measurement device, as a pressure applied by the measurement device is varied across a range of pressures:

extract from said arterial volume signal a signal indicative of a peak-to-peak amplitude of the arterial volume across said range of applied pressures;

acquire using the means for measuring pulse arrival time a signal indicative of a variation in pulse arrival time at a particular location along said artery as said applied pressure is varied across said range of pressures;

derive from said extracted peak-to-peak volume amplitude signal, a signal, $V_{a\text{-}osc}$, indicative of arterial volume as a function of arterial transmural pressure, based on a first model fitting procedure employing a pre-determined arterial volume model; and derive an output measure indicative of arterial compliance based on the derived $V_{a\text{-}osc}$ signal and based on the acquired signal indicative of variation in pulse arrival time, using a further model fitting procedure employing a pre-determined pulse arrival time model relating variation in pulse arrival time, arterial volume, and arterial compliance.

Embodiments of the invention are based on deriving a more robust measure of arterial compliance by combining arterial volume data acquired using oscillometry blood pressure measurements with pulse arrival time data. Pulse arrival time at a location downstream of the oscillometry measurement device can be related to pulse wave velocity along the artery using a simple formula relationship. Pulse wave velocity is known to be employable as a surrogate or proxy for arterial compliance, and can be related to arterial compliance and arterial volume using a known model.

Hence it can be seen that using model fitting approaches, the various gathered information of arterial volume, arterial compliance and pulse arrival time can be combined to derive a measure of arterial compliance.

Since secondary parameters, rather than direct imaging, are used to derive the compliance measure, more long-term or ongoing monitoring is rendered much more straightforward.

Improved robustness of the compliance measure is achieved through two features, both of which reduce the noise in the final compliance measure.

Firstly, rather than using the whole arterial volume waveforms in the final derivation of the compliance measure, only maximum and minimum values (via the peak-to-peak amplitude) are utilized. This avoids carrying through into the compliance measure any noise which is present throughout the rest of the continuous signal.

Secondly, due to the very different modalities represented by oscillometry and pulse arrival time measurements, the two measurements are vulnerable to different sources and types of noise. By combining data acquired using both therefore, the two can supplement one another in a complementary way, reducing the effects of any noise present in either signal.

Determining compliance requires knowledge of the variation in the arterial volume as a function of changing transmural pressure. The first model fitting procedure is used to transform the extracted volume amplitude signal into a corresponding arterial volume—transmural pressure function.

In use, the artery is assumed to be beneath the oscillometric blood pressure measurement device. For example in use, the oscillometric measurement device is mounted to a part of a subject's body, covering said given artery. For example, mounted to the arm, and where the artery is the Brachial artery.

In use, the means for measuring pulse arrival time is assumed to be fitted to the body in a suitable configuration and location for measuring variation in pulse arrival time at said particular location along the same artery whose volume variation is measured by the oscillometric device. For example, the means for measuring pulse arrival time may comprise at least a PPG sensor, and the PPG sensor may in use be fitted to a finger of the subject, downstream from an oscillometric blood pressure measurement device fitted to the arm of the subject.

Pulse arrival time (PAT) in general means the transit time of a blood pulse from the heart to the point at which PAT is measured.

The oscillometric blood pressure measurement device may comprise an inflatable cuff. The device may comprise an internal pressure sensor for measuring a pressure inside an inflation (air) chamber of the cuff.

The oscillometric blood pressure measurement device may be a sphygmomanometer for example.

Pulse arrival time (PAT) may be measured relative to a particular feature, such as a peak, of a measured ECG signal of the subject. For example, the pulse arrival time may be measured as the time interval between the R-peak of an ECG signal and a signal peak of a PPG sensor.

The acquired signal indicative of variation in pulse arrival time may be represented as a waveform representing pulse arrival time as a function of applied pressure, or as a function of a different variable, such as time. The requirement is simply that the signal is representative of a variation in the pulse arrival time over a period when the applied pressure is being varied.

The signal indicative of variation in arterial volume of the artery is acquired as pressure applied to the artery by the measurement device is varied across a range of pressures. The acquired signal may be represented as a waveform representing arterial volume as a function of applied pressure, or as a function of a different variable, such as time. The requirement is simply that the signal is a variation in the arterial volume over a period when the applied pressure is being varied.

The arterial volume oscillates up and down in value with each heart cycle. Peak-to-peak volume amplitude means the difference between the maximum and minimum values of the arterial volume signal at each point along signal. This can be understood as the height of the envelope of the (oscillating) arterial volume signal.

The peak-to-peak amplitude hence means the difference between the maximum and minimum values of arterial volume in a given cycle. The signal indicative of peak-to-peak amplitude of arterial volume means therefore a signal indicative of this difference between the maximum and minimum arterial volume across the range of applied pressures, i.e. for each cycle across the range of applied pressure.

The peak-to-peak volume amplitude signal may be represented by a waveform representing the variation in peak-to-peak amplitude of the arterial volume as a function of the changing applied pressure, or as a function of a different variable such as time. The requirement is simply that the signal is a variation in the peak-to-peak amplitude of the arterial volume over that period when the applied pressure is being varied.

According to certain examples, the pulse arrival time model may be based on a first relationship between pulse arrival time and pulse wave velocity, and a second relationship between pulse wave velocity, arterial volume and arterial compliance.

In examples, the $V_{a\text{-}osc}$ signal may be used to inform fitting of the pulse arrival time model. It may be used as constraint on the fitting for example, for example as a constraint on the parameters on the fitting.

According to an advantageous set of examples, the further model fitting procedure may comprise:
iteratively generating different sample functions of arterial volume as a function of transmural pressure and of arterial compliance as a function of arterial pressure; generating, using the pulse arrival time model, a corresponding modeled function of pulse arrival time, for each sample arterial volume function, and in each case comparing the resulting modeled function of pulse arrival time with the acquired variation in pulse arrival time.

In this way the measured pulse arrival time information can be used to inform or guide the fitting of the pulse arrival time model. Once the model is fitted, since it relates PAT also to compliance, a measure of compliance can be derived.

The different sample functions of arterial volume may be generated using an arterial volume model, relating arterial volume and arterial transmural pressure.

The arterial volume model may take the general form for instance $$V(P_{tm}) = d \cdot L \cdot \frac{\ln(a * P_{tm} + 3.3)}{\left(1 + e^{-c * P_{tm}}\right)},$$

where $V(P_{tm})$ is arterial volume as a function of arterial transmural pressure, a, c and d are fitting parameters for the model, $P_{tm}$ is transmural pressure and L is a length of a body-contacting portion of the oscillometric measurement device.

The different sample functions of arterial compliance may in examples be generated by taking the derivative of the different sample functions of arterial volume with respect to arterial transmural pressure.

The further model fitting procedure referred to above may, according to one or more sets of examples, comprise:
deriving a signal indicative of arterial compliance by differentiating the derived $V_{a\text{-}osc}$ signal with respect to transmural pressure;
generating a modeled pulse arrival time function, $\Delta PAT_{osc}$, by substituting the derived $V_{a\text{-}osc}$ signal and the derived signal indicative of arterial compliance into the pulse arrival time model; and comparing each of the generated model pulse arrival time functions of claim 5 with the modeled pulse arrival time function $\Delta PAT_{osc}$.

This represents one means by which the arterial volume signal $V_{a\text{-}osc}$ derived using the oscillometric measurement device can be incorporated into the deriving of the output arterial compliance measure. In particular, because the pulse arrival time model relates PAT to arterial volume and arterial compliance, from the oscillometric $V_{a\text{-}osc}$ signal (and corresponding compliance signal, generated by taking the derivative with respect to transmural pressure), can be used to derive a PAT function. This can be compared with each of the above mentioned sample model pulse arrival time functions generated using sample $V_{art}$ and compliance functions.

The comparison may comprise performing a similarity assessment. It may comprise deriving a measure of similarity. This may be based on a Bayesian approach for instance. This will be explained in more detail below.

The results of the comparison may guide the model fitting procedure. For example, the model fitting procedure may be iterative, based on generating and sampling in the model different sample functions of arterial volume as a function of arterial transmural pressure.

The pulse arrival time model may in advantageous examples have the form:

$$\Delta PAT(P_{tm}) = \left( \frac{1}{PWV(P_{tm})} - \frac{1}{PWV_{ref}} \right) \cdot L$$

where $$PWV(P_{tm}) = \sqrt{\frac{V(P_{tm})}{\rho C(P_{tm})}}$$

where $PWV(P_{tm})$ is pulse wave velocity as a function of transmural pressure, $\Delta PAT$ is variation in pulse arrival time, $V(P_{tm})$ is arterial volume as function of transmural pressure, $C(P_{tm})$ is arterial compliance as function of transmural pressure, $\rho$ is blood density, and L is the length of a body-contacting portion of the oscillometry measurement device. L may be more particularly a length of the portion of the device which adapted in use to apply a varying pressure to the artery.

$PWV_{ref}$ is the pulse wave velocity at $P_{tm}$=MAP, where MAP is mean arterial pressure. Mean arterial pressure is the mean (or baseline) arterial pressure within the artery when the cuff is not applying any external pressure. This can be derived from an arterial pressure signal $P_{art}$ extracted from internal cuff pressure measurements during the measurement process. It may be the baseline value of this signal for example. This will be described in greater detail below. Hence, $PWV_{ref}$ may be given by $$PWV_{ref} = \sqrt{\frac{V(MAP)}{\rho C(MAP)}}.$$

This model uses the well-known Bramwell-Hill model $$PWV(P_{tm}) = \sqrt{\frac{V(P_{tm})}{\rho C(P_{tm})}},$$

but also utilises a relationship between PAT and PWV. PAT is in many scenarios easier to measure directly than PWV. PWV requires knowledge of the length travelled by the pulse and of the heart pre-ejection period, which are difficult to measure. The above model allows the simpler PAT to be measured.

The means for measuring a pulse arrival time may comprise an ECG sensor device and a PPG sensor. The pulse arrival time may be derived as the difference in time between the R-peak of the ECG signal and a particular characteristic point (e.g. a peak) in the PPG signal. In use, the PPG sensor may be attached a finger of the subject, along the same arm to which an inflatable cuff of the blood pressure measurement device is mounted. In this way pulse arrival time is measured preferably along the same artery as is being pressured by the blood pressure measurement device.

The acquiring of the signal indicative of arterial volume variation may comprise controlling an inflatable cuff of the oscillometric measurement device to gradually inflate to thereby vary said applied pressure to the artery beneath the cuff through said range of pressures.

An arterial volume measurement signal may then be simultaneously acquired using the measurement device.

The variation in pulse arrival time across said range of transmural pressures may comprise monitoring variation in pulse arrival time as said cuff is gradually inflated. The acquiring of the signal indicative of arterial volume variation may comprise sensing a pressure variation within an inflatable cuff of the oscillometric measurement device, and deriving an arterial volume measure based on the sensed pressure variation and a known elasticity of the cuff.

The pressure variation may be assumed to occur for a given fixed inflation level/volume of the cuff, i.e. so that variation in pressure is fully attributable to increasing/decreasing volume of an artery beneath the cuff, varying an applied pressure to the cuff.

In examples, the first model fitting procedure may comprise:
 generating different sample functions of arterial volume as a function of transmural pressure using said arterial volume model;
 extracting from each sample function a corresponding sample signal representative of variation in peak-to-peak amplitude of arterial volume across said range of applied pressures; and
 comparing each sample peak-to-peak volume amplitude signal with the extracted volume amplitude signal extracted from the measured arterial volume signal.

The first modeling procedure effectively allows the initially extracted volume amplitude signal to be transformed into an arterial volume signal, expressed as a function of transmural pressure. This results in an arterial volume-transmural pressure function (the $V_{a\text{-}osc}$ signal). From this, compliance information is derivable (as the derivative with respect to transmural pressure).

The results of the comparison may be used to guide the model fitting. In particular, the results of the comparison may be used to iteratively guide the iterative generation of further sample arterial volume functions. For instance, the parameters of the model may be iteratively adjusted according to the comparison outcome, so that future generated functions of arterial volume have amplitude signals which more closely match the acquired measured arterial volume information.

In this way, generating of each new sample function of arterial volume may be guided by the results of the previous comparison in an iterative approach. In this way, parameters of the arterial volume model are iteratively optimized.

According to one set of advantageous examples, the pre-determined arterial volume model may be based on a relation having the form $$V(P_{tm}) = d \cdot L \cdot \frac{\ln(a * P_{tm} + 3.3)}{\left(1 + e^{-c*P_{tm}}\right)},$$

where $V(P_{tm})$ is arterial volume as a function of arterial transmural pressure, a, b and c are fitting parameters for the model, $P_{tm}$ is transmural pressure and L is a length of a body-contacting portion of the oscillometric measurement device. L may be more particularly a length of the portion of the device which adapted in use to apply a varying pressure to the artery.

Examples in accordance with a further aspect of the invention comprise a method of deriving a measure of arterial compliance, comprising:

acquiring using an oscillometric measurement device a signal indicative of variation in arterial volume of an artery located beneath the measurement device, as an applied pressure to the artery by the oscillometric measurement device is varied across a range of pressures;

extracting from said arterial volume signal a signal indicative of a variation in peak-to-peak amplitude of arterial volume across said range of applied pressures;

acquiring using a means for measuring pulse arrival time a signal indicative of a variation in pulse arrival time at a particular location along said artery as said arterial transmural pressure is varied by the oscillometric measurement device across said range of pressures;

deriving from said extracted peak-to-peak volume amplitude signal, a signal, $V_{a\text{-}osc}$, indicative of arterial volume as a function of arterial transmural pressure, based on a model fitting procedure employing a pre-determined arterial volume model; and deriving an output measure indicative of arterial compliance based on the derived $V_{a\text{-}osc}$ signal and based on the acquired variation in pulse arrival time, the deriving being based on a further model fitting procedure employing a pre-determined pulse arrival time model relating variation in pulse arrival time, arterial volume, and arterial compliance.

In examples, the method may further comprise a preliminary step of fitting the oscillometric measurement device to a part of a subject's body, with the device positioned above an artery for applying a variable pressure to said artery.

The method may in examples further comprise a preliminary step of fitting the means for measuring pulse arrival time to the body in a suitable configuration and location for measuring variation in pulse arrival time at said particular location along the same artery whose volume variation is measured by the oscillometric device. For example, the means for measuring pulse arrival time may comprise at least a PPG sensor, and the PPG sensor may be fitted to a finger of the subject, downstream from an oscillometry device fitted to the arm of the subject.

The artery to which the blood pressure measurement device is applied may be the brachial artery in examples.

Examples in accordance with a further aspect of the invention provide a system for deriving a measure of arterial compliance, comprising:

a control unit in accordance with any example or embodiment described above or below, or in accordance with any claim of this application;

an oscillometric blood pressure measurement device operatively coupled to the control unit; and means for measuring a pulse arrival time, operatively coupled to the control unit.

The system preferably further comprises a display operatively coupled to the control unit, the control unit adapted to control the display to generate a visual output representative of the derived arterial compliance measure.

The control unit may derive compliance values recurrently, for instance in real-time fashion. The values may be displayed in real time on a provided display.

The system may include means for communicating or operatively coupling with further sources of patient information, such as further physiological parameter sensing units, and to store, process and/or display said additional patient information, for instance in addition to the arterial compliance information.

According to a further set of embodiments, the system may further comprise a patient monitor unit, and wherein the patient monitor unit comprised the control unit. The control unit may be accommodated within the patient monitor unit, or may alternatively be functionally integral with it so that the functionality of the control unit is performed by the patient monitor unit. The oscillometric blood pressure measurement device may be operatively coupled to the patient monitor unit. The means for measuring pulse arrival time may be operatively coupled to the patient monitor unit.

The patient monitor unit may be adapted to communicate or operatively couple with further sources of patient information, such as further physiological parameter sensing units, and to store, process and/or display said additional patient information, for instance in addition to the arterial compliance information. The patient monitor unit may include a display for displaying the additional information and/or the derived compliance measure.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a control unit and method for deriving a measure of arterial compliance based on an acquired arterial volume variation signal and an acquired pulse arrival time signal. An oscillometric blood pressure measurement device is used to acquire the arterial volume variation signal. Arterial volume and variation in pulse arrival time are both measured as an applied pressure to an artery are varied by the oscillometric blood pressure measurement device. The arterial volume signal is transformed into a corresponding signal representative of variation in peak-to-peak amplitude of the arterial volume. A first model fitting procedure is used to transform this peak-to-peak amplitude signal into a signal indicative of arterial volume as a function of transmural pressure. A second model fitting procedure is used to generate from the derived arterial volume vs. transmural pressure signal, and the derived pulse arrival time variation signal a final output measure of arterial compliance.

By fusing information obtained from two different modality sources (arterial volume and PAT), more reliable estimation of arterial compliance is obtained. This permits, inter alia improvement in the following applications:

Earlier detection of patient deterioration: changes in arterial compliance often precede large changes in blood pressure and hemodynamic instability.

Diagnosis and treatment of cardiovascular diseases: measurement of arterial compliance can play a role in assessment of cardiovascular disease progression and in evaluation of patient responsiveness to treatment.

Improved accuracy of calibration of blood pressure surrogate measures such as pulse arrival time and pulse morphology features.

Accurate and, for instance, long-term or ongoing or continuous measurement of arterial compliance also may at least partially assist in the development of personalized medical procedures, since arterial compliance is one useful factor in better identifying different patient groups, e.g. groups distinguished in terms of medication responses.

Figure 1:
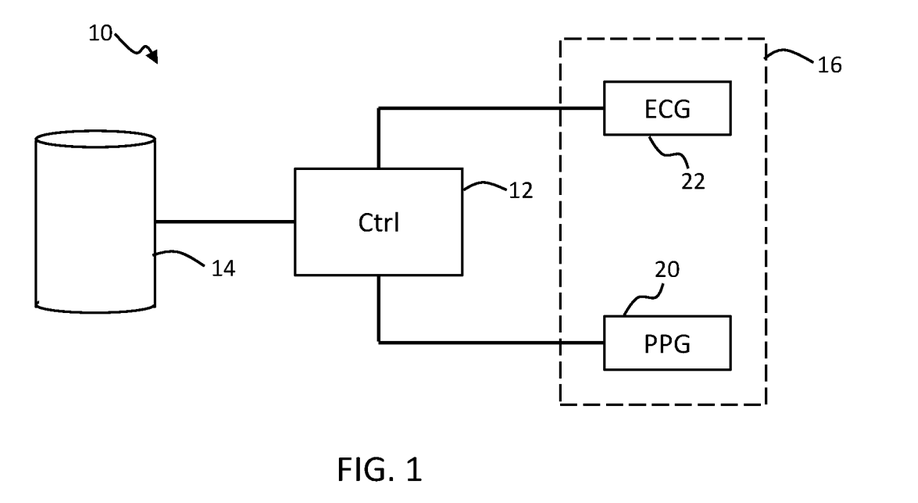
FIG. 1 shows a block diagram of an example control unit and system according to one or more embodiments of the invention.

FIG. 1 shows an example control unit 12 according to one or more embodiments of the invention. The control unit is configured to derive a measure of arterial compliance. The control unit is operably coupleable in use with an oscillometric blood pressure measurement device 14, and a means for measuring pulse arrival time 16.

For illustration, the control unit is shown in FIG. 1 when in use, coupled to an oscillometric blood pressure measurement device 14 and to a means for measuring pulse arrival time 16. The means for measuring pulse arrival time 16 comprises in this example an ECG sensor device 22 and a PPG sensor 20.

FIG. 1 hence illustrates a complete system 10 for deriving a measure of arterial compliance. According to one aspect of the invention the control unit 12 may be provided alone. In another aspect, the system 10 may be provided, including the control unit and the blood pressure measurement device 14 and means 16 for measuring pulse arrival time. The control unit 12 is adapted to perform a series of steps which when performed result in deriving of an output measure indicative of arterial compliance. The series of steps performed by the control unit 12 will now be outlined in summary, followed by a more detailed explanation of example implementation of the steps, with reference to further figures.

The control unit 12 is adapted to acquire using the oscillometric blood pressure measurement device 14 a signal indicative of a variation in arterial volume of an artery assumed to be in contact with the measurement device, as a pressure applied to the artery by the measurement device is varied across a range of pressures. In the context of this application, the contact, in which the artery assumed to be with the measurement device, is meant to be in a broader sense, which includes non-direct (non-invasive) manner, wherein some of the measurement device's properties are affected by the volume variation of the artery.

The control unit 12 may control the oscillometric measurement device 14 to vary the applied pressure through said range of pressure. Alternatively the oscillometric blood pressure measurement device 14 may incorporate a local controller for controlling the applied pressure variation, or a further auxiliary controller may be provided for controlling the pressure for instance.

In brief, the measurement device may include an inflatable cuff. The cuff in use may be gradually inflated so as to increase a pressure applied to the artery through a range of ever-increasing pressures. Alternatively, the cuff may in use be inflated to fully occlude the artery in question before the applied pressure is gradually reduced through a range of decreasing applied pressures.

In either case, the cuff is adapted to sense arterial volume oscillations of the artery as applied pressure is varied. These volume oscillations naturally depend on arterial compliance (distension of the artery wall in response to transmural pressure changes).

In particular, this may be done by measuring changes, e.g. oscillations, in internal pressure within an inflation chamber in the cuff. For a given (fixed) cuff inflation, such oscillations can be taken to be representative of variations in pressure applied to the cuff by the underlying artery as it pulses with blood. If the compliance (elasticity) of the cuff is known, this can be converted into a signal indicative of volume variations of blood within the artery at each of the range of different applied pressures. Other pressure sensing means could be used in further examples, for instance simply a contact pressure sensor or transducer arranged to sense pressures applied to a surface of the cuff.

The control unit is further adapted to extract from said arterial volume signal a signal indicative of a peak-to-peak amplitude of the arterial volume across said range of applied pressures. Peak-to-peak volume amplitude signal means a signal which represents variation in the total "height" of the envelope of the arterial volume signal acquired in the first step above. Envelope here is used in its normal meaning when applied to a signal, and corresponds for instance to a pair of smooth curves outlining the extremes of the volume signal.

The volume amplitude signal hence effectively corresponds to the variation in the total change in arterial volume between systole and diastole phases, across said range of applied pressures.

The control unit 12 is further adapted to acquire using the means for measuring pulse arrival time (PAT) 16 a variation in pulse arrival time at a particular location along said artery as said applied pressure is varied across said range of pressures. For example, pulse arrival time may be measured at a finger of the patient along the same arm as the blood pressure measurement device is applied to. Pulse arrival time means the transit time of a blood pulse from the heart to the point at which arrival time is measured. Pulse arrival time may be derived for example from a time difference between the R-peak of an acquired ECG signal waveform and a particular peak point in an acquired PPG signal.

The PAT is thus measured as the applied pressure is varied during an oscillometric measurement. As the applied pressure increases, the transmural pressure along the length of the measurement device (e.g. cuff) is altered and the PAT varies. The variation in pulse arrival time is indicative of elasticity characteristics of the artery for a range of transmural pressures, and the information can thus be used to derive arterial compliance information. This will be described in greater detail below.

The control unit 12 is further adapted to derive from said extracted peak-to-peak volume amplitude signal, a signal, $V_{a-osc}$, indicative of arterial volume as a function of arterial transmural pressure, based on a first model fitting procedure employing a pre-determined arterial volume model. This is explained in greater detail below.

The control unit 12 is further to derive an output measure indicative of arterial compliance based on the derived $V_{a-osc}$ signal and based on the derived variation in pulse arrival time, using a further model fitting procedure employing a pre-determined pulse arrival time model which relates variation in pulse arrival time, arterial volume, and arterial compliance.

This second arterial model hence allows for linking together all of the acquired information and permits a derivation of an output measure of arterial compliance using all of the acquired parameters.

Output information may be generated representative of the derived measure of arterial compliance. This output information may be communicated by the control unit to an external device or computer or processor, for instance by transmission of a data message representative of the output information.

Figure 2:
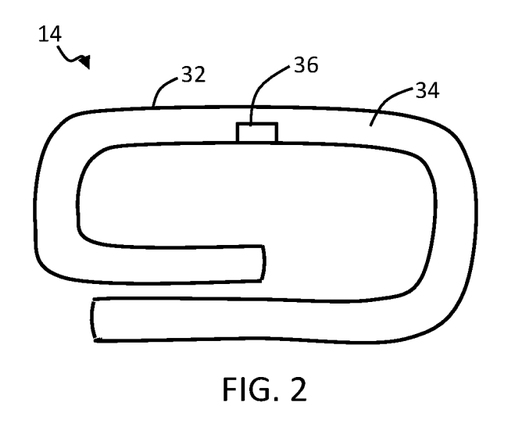
FIG. 2 illustrates an example inflatable cuff of an example oscillometric blood pressure measurement device.

FIG. 2 shows a cross-sectional view through an example oscillometric blood pressure measurement device 14 which may in examples be used with the control unit in use for deriving the measure of arterial compliance.

The oscillometric measurement device 14 in this example is in the form of a sphygmomanometer.

The example oscillometric measurement device 14 comprises an inflatable cuff 32 with an internal air chamber 34 with a volume which can be varied to change an inflation level. The air chamber can in other examples be any fluid chamber. The internal air chamber accommodates an air pressure sensor 36 which senses an internal cuff pressure.

In use, the inflatable cuff is wrapped around a part of a subject's body, most typically the upper arm, such that the cuff overlies, and is arranged for applying pressure to, an artery included in said part of the body.

Figure 3:
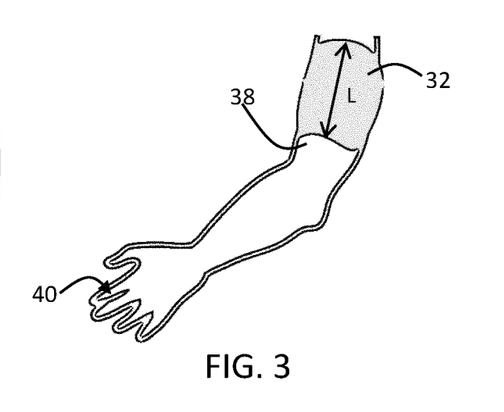
FIG. 3 illustrates an example oscillometric blood pressure measurement device in use.

This is illustrated in FIG. 3 which shows the cuff 32 applied to the upper arm 38. In this case the cuff overlies the Brachial artery.

In use, the cuff is inflated until the artery is completely occluded. The pressure applied by the cuff is then gradually decreased through a range of decreasing applied pressures, and the internal cuff pressure simultaneously (and preferably continuously) measured. As discussed in more detail below, this information is used to derive a signal indicative of the arterial volume variations. Alternatively, the cuff may instead be gradually inflated, so that pressure applied by the cuff to the artery is gradually increased through a range of increasing applied pressures. In either case, the applied pressure is transitioned through a range of changing applied pressures, where these may be either increasing or decreasing pressures.

Although in the above example, the oscillometric blood pressure measurement device is a sphygmomanometer type device comprising an inflatable cuff, this represents just one advantageous example. Any alternative form of oscillometric blood pressure measurement device may alternatively by used. The measurement device is preferably capable of applying a varying applied pressure to an artery of a subject in use. This may be through any pressure application means.

The means for measuring pulse arrival time 16 comprises in this example an electrocardiogram (ECG) sensor device 22 and a photoplethysmogram (PPG) sensor 20. The ECG sensor device comprises a pair of electrodes (not shown) which in use are affixed spaced apart from one another to a patient's skin. Typically the electrodes are positioned either side of the patient's heart. The electrodes of the ECG sensor detect electrical signals produced by the heart each time it beats. By monitoring these signals, a signal indicative of heart activity is derived.

The theory and operation underlying ECG sensors is well known in the field and will not be outlined in detail. The skilled person will be aware of means for providing, and operating an ECG for acquiring an ECG electrical signal.

The PPG sensor 20 comprises a light source (e.g. an LED light source) which in use illuminates the skin and measures the change in light absorption. This form of PPG is known as a pulse oximeter. Other kinds of PPG will be known to the skilled person and may alternatively be used.

Photoplethysmography (PPG) is an optical measurement technique that evaluates a time-variant change of light reflectance or transmission of an illuminated area. PPG is based on the principle that blood absorbs light more than surrounding tissue, so variations in blood volume or blood pressure (e.g. with every heartbeat) affect transmission or reflectance correspondingly. By detecting changes in detected blood-related signals, a cyclic signal corresponding to the pulse can be obtained.

The ECG sensor device 22 and the PPG sensor together provide a means for measuring pulse arrival time. The pulse arrival time may for example be derived based on a time difference between two characteristic peaks or signal features of signals output by the ECG and PPG.

For example, in use, the PPG sensor 20 may be mounted on a finger of the subject, along the same arm as the blood pressure measurement device is placed (for example, and by way of illustration only, the finger indicated by arrow 40). Fiducial points on the ECG and PPG signals can then be used to derive a measurement of pulse transit time along the artery For example, a peak in the PPG signal may indicate arrival of a blood pulse at the finger. A peak (e.g. the R-peak) of the ECG signal may indicate end-systole, and hence the originating time of the pulse to be later detected at the finger. A difference between these signal peaks may be used as a measure of pulse arrival time.

The control unit 12 may be adapted in use to control, e.g. issue control commands to, the oscillometric blood pressure measurement device, and the means for measuring pulse arrival time, to acquire said signal indicative of variation in arterial volume of an artery and said variation in pulse arrival time. Alternatively the oscillometric blood pressure measurement device 14 and/or ECG sensor device may each incorporate a local controller for controlling the respective signal acquisitions, or a further auxiliary controller may be provided for this purpose, either shared between the sensor devices, or one controller for each.

It is noted that although in the above example, the example blood pressure cuff 32 incorporates an air pressure sensor 36 for sensing the pressure oscillations caused by the artery to the cuff, in other examples other means can be used to sense the changes in the pressure applied to the cuff by the artery 48. These include for instance a contact pressure sensor mechanically communicating with the wall 52 of the cuff for directly sensing the changing pressure applied to the wall by the artery as it waxes and wanes. In other examples, a transducer such a microphone may be used to sense vibrations in the wall caused by the pressures exerted.

The steps outlined in brief above for acquiring arterial volume variation information, pulse arrival time and output arterial compliance information will now be described in more detail. These will be described by way of reference to a particular example implementation in the steps outlined below. This is presented by way of example only, for the purpose of demonstrating the concepts of the invention, and is not limiting of the inventive concept in general.

Figure 4:
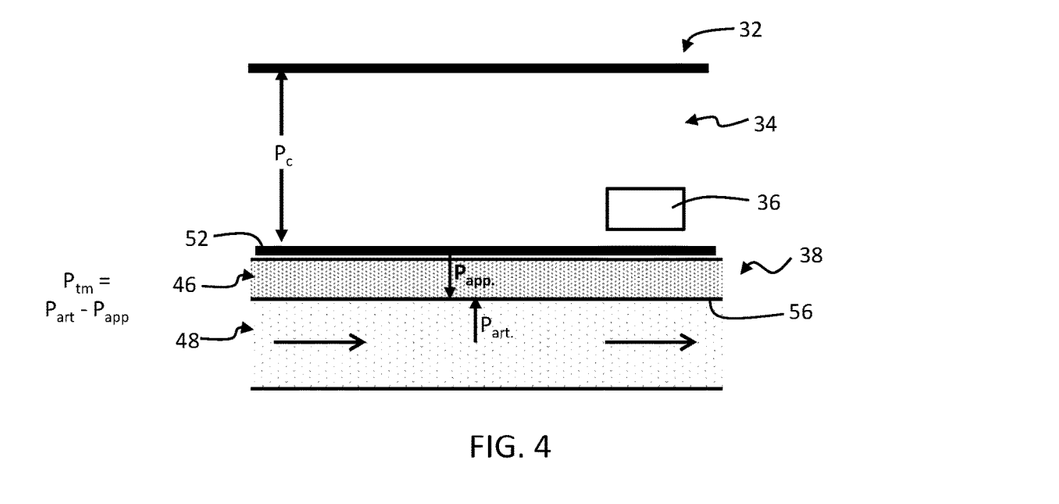
FIG. 4 illustrates a cross-section through an example artery and applied inflatable blood pressure measurement cuff.

FIG. 4 shows a cross-sectional illustration of application of an example oscillometric blood pressure measurement device (in the form of an inflatable cuff 32) to an example section of an upper arm 38 of a subject. In particular, only an upper-most layer part of the subject's arm is shown, comprising the brachial artery 48 (by way of example) and an overlying layer of arm tissue 46.

An outer wall 52 of the cuff is shown applied to the upper surface of the arm. An internal air chamber 34 of the cuff is illustrated, and a pressure sensor 36 is accommodated within the cuff air chamber adapted to measure a cuff air pressure $P_c$ inside the air chamber. This pressure inside the chamber will be referred to for brevity as 'cuff pressure', $P_c$.

The cuff pressure $P_c$ is the pressure exerted internally within the cuff air chamber 34 on internal surfaces of the walls 52 of the cuff chamber 34.

In operation, the inflatable cuff 32 is fitted to the subject (for instance to the upper arm), by wrapping snugly around the arm.

The cuff is then gradually inflated by gradually increasing a volume inside the cuff inflation chamber 34, thereby gradually increasing the internal cuff pressure $P_c$.

As the cuff is inflated, it exerts an increasing applied pressure, Papp, to the artery 48, via the upper tissue layer 46. This pressure applied by the cuff to the artery 48 wall will be referred to for brevity as the applied pressure, $P_{app}$.

The applied pressure, $P_{app}$, is the pressure applied by the cuff to the boundary wall 56 of the artery 48.

The applied pressure, $P_{app}$, is often assumed to be approximately equal to the internal cuff pressure $P_c$, (or for instance a baseline value of the internal cuff pressure) i.e. the pressure inside the inflation chamber of the cuff. Internal cuff pressure may thus be used as a measure of applied pressure in some examples.

Inside the artery 48, blood flows along the lumen, pumped from the heart. The internally flowing blood exerts a pressure outward onto the interior surfaces of the boundary walls 56 of the artery 48. This pressure will be referred to as the arterial pressure, $P_{art}$, and is indicated by an arrow in FIG. 4.

The arterial pressure, $P_{art}$, oscillates up and down in value each heart cycle. The pressure reaches a maximal level at end systole, and falls to a minimum value at end diastole. These maximum and minimum arterial pressure values, associated with the different phases of the heart, are known as systolic arterial blood pressure $P_{sys}$ and diastolic arterial blood pressure $P_{dia}$ respectively.

The transmural pressure $P_{tm}$ across the artery wall 56 is equal to the difference between the arterial pressure $P_{art}$ and the applied pressure $P_{app}$. This can be expressed as $$P_{tm} = P_{art} - P_{app}$$

In operation, the cuff is gradually inflated by gradually increasing a volume inside the cuff inflation chamber 34, thereby gradually increasing the internal cuff pressure $P_c$. This results in a gradually increasing applied pressure $P_{app}$ to the artery 48.

Figure 5:
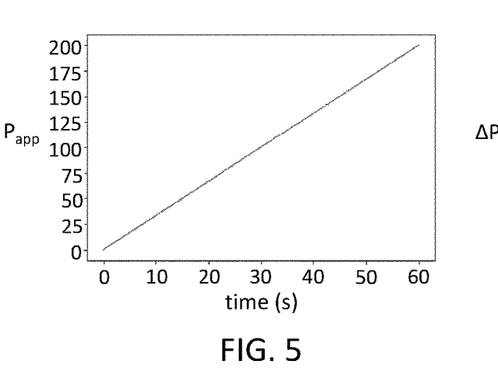
FIG. 5 shows cuff applied pressure as a function of time in an example implementation of a control unit according to one or more embodiments.

FIG. 5 shows the variation in applied pressure $P_{app}$ as a function of time for one example implementation. The y-axis shows applied pressure $P_{app}$ (units: mmHg) and the x-axis shows time in seconds, relative to a start of the measurement operation.

At the minimum applied pressure, the artery 48 is fully open for example. At the maximum applied pressure the artery is fully occluded for example.

As the applied pressure, $P_{app}$, is increased, the artery becomes increasingly compressed by the cuff, thereby reducing a local internal diameter of the artery 48 lumen. The artery is thus gradually transitioned from completely open to completely occluded. The local arterial pressure at the part of the artery wall 56 being compressed oscillates with certain amplitudes depending upon the transmural pressure at a given time, and upon the systolic and diastolic arterial blood pressure values in the absence of any occlusion.

The oscillations in arterial pressure $P_{art}$ can be sensed at the inflatable cuff 32 of the blood pressure measurement device since they exert an oscillating pressure to the wall 52 of the cuff inflation chamber 34. This oscillating pressure leads to small local oscillations in internal cuff pressure $P_c$. These oscillations are superposed on the background or baseline internal cuff pressure, and are sensed by the cuff pressure sensor 36.

By sensing the amplitude of the cuff pressure $P_c$ oscillations, the arterial pressure $P_{art}$ oscillations as a function of time can be extracted. This will now be further explained with reference to FIG. 6.

Figure 6:
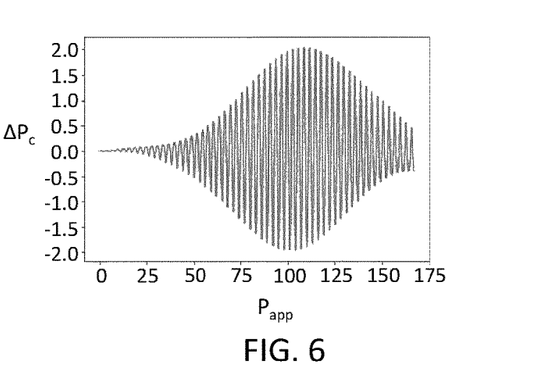
FIG. 6 shows oscillations in internal inflation chamber pressure of an inflatable cuff as a function of time in an example implementation of a control unit according to one or more embodiments.

FIG. 6 shows a waveform representing example de-trended oscillations in cuff pressure $P_c$ (y-axis: mmHg) as would be sensed inside the inflation chamber 34 of the inflatable cuff 32 as a result of the locally oscillating arterial pressure $P_{art}$. The oscillations are de-trended, meaning extracted from the overall varying global (or baseline) pressure inside the cuff chamber, varying due to the cuff's gradual inflation. Hence the cuff pressure oscillation value of 0 in the illustrated waveform is calibrated as being equal to the baseline total cuff pressure regardless of inflation level. The oscillations in cuff pressure $\Delta P_c$ (y-axis) are shown as a function of cuff applied pressure $P_{app}$ (x-axis: mmHg).

From these sensed internal oscillations in cuff pressure $\Delta P_c$, the local arterial pressure $P_{art}$ oscillations can be derived. One subset of the corresponding arterial pressure oscillations for the shown example $P_c$ oscillations are illustrated by the waveform in FIG. 7 (y-axis: arterial pressure, units mmHg: x-axis: time: units seconds). The upper peaks of the oscillations correspond to the systolic arterial pressure $P_{sys}$, while the lower troughs of the oscillations correspond the diastolic arterial pressure $P_{dia}$.

Deriving arterial pressure $P_{art}$ oscillations from measured internal oscillations in cuff pressure $\Delta P_c$, may be performed using for instance a conversion algorithm or for instance a suitable empirical or mathematical model. One suitable technique for deriving the arterial pressure oscillations from cuff pressure oscillations is described in detail in the paper: F Babbs, Charles. (2012). Oscillometric measurement of systolic and diastolic blood pressures validated in a physiologic mathematical model. Biomedical engineering online. 11. 56. 10.1186/1475-925X-11-56. This model has been shown to derive $P_{art}$ measurements which correspond closely with measured Pan values derived using more classical invasive measurement means.

This technique represents just one example, and there are many other suitable algorithms which have been developed for deriving Pan variation from internal oscillometric cuff pressures, as will be known to the skilled person.

Figure 7:
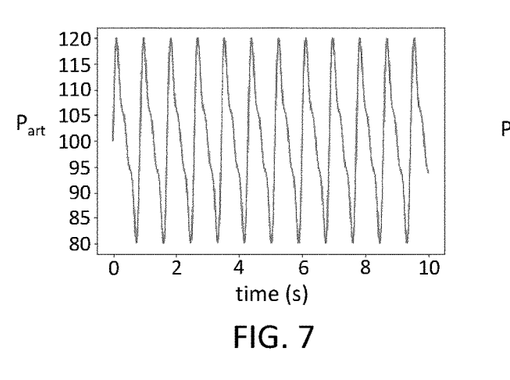
FIG. 7 shows arterial pressure oscillations as a function of time in an example implementation of a control unit according to one or more embodiments.

From these derived arterial blood pressure $P_{art}$ oscillations of FIG. 7 and the known applied pressure $P_{app}$ variation as a function of time (shown in FIG. 5), oscillations in local transmural pressure $P_{tm}$ across the artery 48 wall can be derived.

Figure 8:
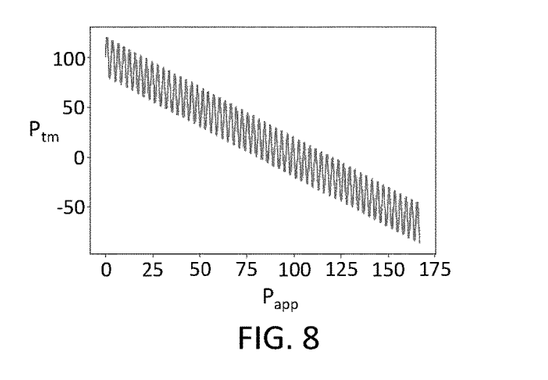
FIG. 8 shows transmural pressure oscillations as a function of time in an example implementation of a control unit according to one or more embodiments

The resulting example waveform representing the corresponding transmural pressure $P_{tm}$ oscillations as a function of cuff applied pressure $P_{app}$ is shown in FIG. 8.

If the compliance, i.e. elasticity, of the cuff 32 is known in advance, the sensed cuff pressure $P_c$ oscillations (shown in FIG. 6) can also be converted into corresponding arterial volume $V_{art}$ oscillations. The local arterial blood pressure oscillations as a function of time are merely a reflection of locally oscillating blood volumes in the compressed section of the artery. These arterial pressure oscillations are directly reflected as oscillations in internal cuff pressure $P_c$ (as explained above, via pressing of the artery on the cuff). Hence, the sensed internal cuff pressure oscillations, $P_c$, can be readily processed into arterial volume oscillations if the cuff elasticity is known.

Figure 9:
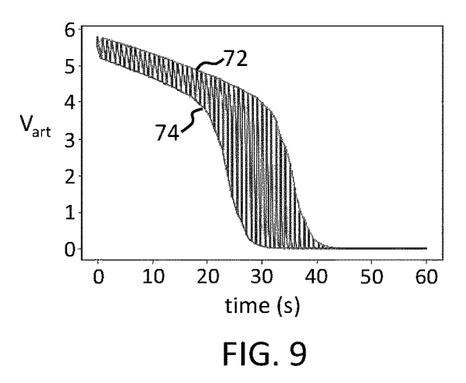
FIG. 9 shows derived arterial volume oscillations as a function of time in an example implementation of a control unit according to one or more embodiments

The resulting signal indicative of variation in arterial volume $V_{art}$ (y-axis; units: ml) for this example is shown in FIG. 9. This signal is shown as a function of time (x-axis; units: mmHg). In other examples however, it may be represented by a signal as a function of a different variable such as applied pressure $P_{app}$. The requirement is simply that the signal represents arterial volume variations or oscillations across that period when the applied pressure is being varied by the blood pressure measurement cuff 32.

As can be seen the signal embodies both the local oscillations in volume between systole and diastole heart phases and also the global downward trend in arterial volume $V_{art}$ as cuff applied pressure $P_{app}$ is increased (see FIG. 5) and the local artery 48 diameter is decreased.

As noted, the signal indicative of variation in arterial volume $V_{art}$ shown in FIG. 9 encompasses rapid local oscillations about a downward trending baseline. The envelope of the local oscillations is highlighted in FIG. 9. In particular, the upper envelope 72 and lower envelope 74 of the signal are indicated.

Processing whole volume waveforms leaves resulting calculations particularly vulnerable to noise in the signal. Accuracy or robustness of resulting compliance measurements can be increased by considering only the upper and lower peaks of the arterial volume oscillations, i.e. the systolic and diastolic volumes, or the upper and lower envelopes of the signal shown in FIG. 9.

Accordingly, the control unit 12 is adapted in use to extract from the signal indicative of variation in arterial volume (in this example, the signal of FIG. 9) a signal indicative of peak-to-peak amplitude of arterial volume across the range of applied pressures. This corresponds to the 'height' of the envelope of the signal of FIG. 9, i.e. the upper envelope minus the upper envelope, as a function of time (in this example). The peak-to-peak volume amplitude signal represents the variation in peak-to-peak amplitude of arterial volume across the range applied pressures $P_{app}$.

Figure 10:
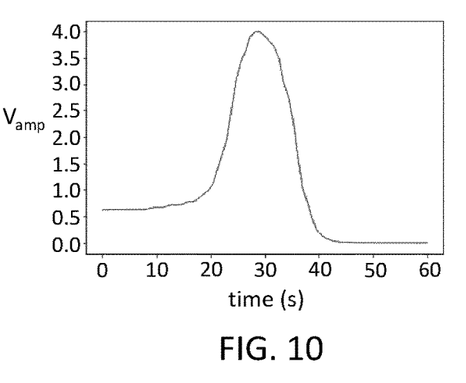
FIG. 10 shows an extracted signal indicative of variation in peak-to-peak amplitude of the arterial volume signal of FIG. 9.

The resulting extracted peak-to-peak amplitude signal (Vamp) for the example arterial volume signal in FIG. 9 is shown in FIG. 10. This shows the peak-to-peak arterial volume amplitude signal, Vamp (y-axis: units: ml) as a function of time (x-axis; units: seconds). However, in other examples, the signal may be represented as a function of a different variable, for example as a function of the applied pressure $P_{app}$. The requirement is simply that the signal is a variation in the peak-to-peak amplitude of the arterial volume over that period when the applied pressure is being varied by the blood pressure measurement cuff 32.

Following extraction of the peak-to-peak arterial volume amplitude signal, the control unit 12 is adapted to derive from said extracted peak-to-peak volume amplitude signal, a signal, $V_{a\text{-}osc}$, indicative of arterial volume $V_{art}$ as a function of arterial transmural pressure $P_{tm}$.

This can be done with a numerical approach. In particular, the volume-transmural pressure relationship is represented with a pre-determined model, and the parameters of the model are found through fitting techniques. In preferred examples, a Bayesian type model fitting approach is used.

Hence, derivation of $V_{a\text{-}osc}$ is performed based on a model fitting procedure, employing a pre-determined arterial volume model.

One example model for arterial volume is represented below $$V(P_{tm}) = d \cdot L \cdot \frac{\ln(a * P_{tm} + 3.3)}{\left(1 + e^{-c * P_{tm}}\right)} \quad (2)$$

where $V(P_{tm})$ is arterial volume as a function of arterial transmural pressure, a, c and d are fitting parameters for the model, $P_{tm}$ is transmural pressure and L is a length of a body-contacting portion of the oscillometric measurement device. In this example, L is a length of the cuff along a direction parallel with the arm on which it is worn. The length of the example cuff shown in FIG. 3 for example is labeled by arrow "L".

The length of the cuff effectively means the length of the section of the artery which the cuff 32 is arranged to apply pressure to. In general, when the cuff is worn this corresponds to an axial length of the cuff. When the cuff is unraveled, in a flat configuration, it will correspond to a shorter of the dimensions of the unraveled cuff, e.g. a width of the unraveled cuff. This is clear from the indicated length dimension "L" in FIG. 3.

The above arterial volume model is based on a model relationship outlined in the paper: Drzewiecki G et al (1994). Theory of the oscillometric maximum and the systolic and diastolic detection ratios. Annals of Biomedical Engineering, 22, pp. 88-96.

It is noted that this represents just one example arterial volume model which may be applied. Many other example models and corresponding equations also exist, as will be apparent to the skilled person. For example, one further suitable example model equation is outlined on page 6 (equations 4a and 4b) of the paper: F Babbs, Charles. (2012). Oscillometric measurement of systolic and diastolic blood pressures validated in a physiologic mathematical model. Biomedical engineering online. 11. 56. 10.1186/1475-925X-11-56.

Returning to equation (2) above, the three fitting parameters a, c, and d may be fitted for example via Markov chain Monte Carlo (MCMC) sampling. Implementation of such a fitting procedure will be well known to the skilled person and will not be outlined in detail in this disclosure.

Detailed explanation of MCMC sampling and data fitting may be found for example in the paper: Hogg, D. W et al, Data analysis recipes: Fitting a model to data, arXiv: 1008.468. A more general detailed overview of the theory underlying Bayesian type model fitting, including MCMC sampling, is found in the book "Doing Bayesian Data Analysis" by John K. Kruschke.

In brief, the model fitting procedure comprises iteratively sampling a series of different sets of parameters for the above arterial volume model (2), comparing extracted peak-to-peak amplitude signals of the resulting sample volume functions to the true peak-to-peak volume amplitude signal derived above, and based on each comparison result, iteratively re-sampling new functions until a sufficiently close match is found.

Prior general knowledge relating to physiological characteristics of the compliance function may be used to inform or constrain the fitting procedure. This prior knowledge or information is expressed in the choice of control parameters. The prior information may constrain the range over which the control parameters may be varied for the fitting for instance.

In more detail, the procedure comprises first generating different sample functions of arterial volume as a function of transmural pressure using the arterial volume model equation (2) above. This involves generating sample sets of parameters a, c and d and substituting these into equation (2) to derive the resulting sample arterial volume function.

The sample functions are generated preferably one at a time, iteratively.

Figure 11:
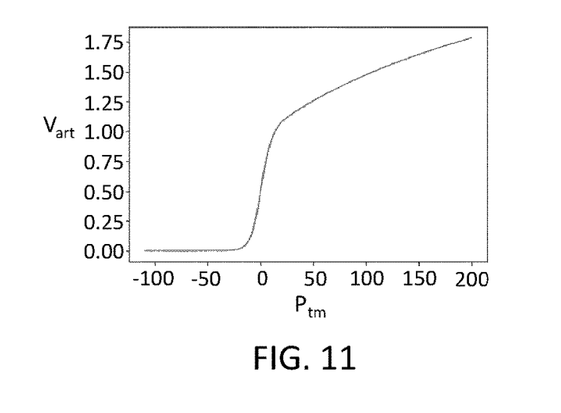
FIG. 11 shows an example derived function of arterial volume as a function of transmural pressure.

One example arterial volume-transmural pressure function is shown in FIG. 11. The y-axis represents arterial volume, $V_{art}$ (units: ml), the x-axis represents transmural pressure $P_{tm}$.

It is necessary to extract from each generated sample volume function a corresponding sample signal representative of variation in peak-to-peak amplitude of the volume, when considered as a function of the changing applied pressure or as a function of time, i.e. a height of the envelope of the volume variation signal when considered as a function of time or applied pressure.

This volume amplitude signal is essentially constructed oscillation by oscillation using the already derived transmural pressure, $P_{tm}$, function (FIG. 8). The transmural pressure function shows how the transmural pressure oscillated across the range of applied pressures. For each oscillation in this signal, the upper and lower transmural pressure values are read. Then the generated sample model $V_{art}$ function is consulted, and the corresponding modeled $V_{art}$ values for each of these upper and lower transmural pressures are identified. These are then subtracted from one another to derive the corresponding peak-to-peak arterial volume amplitude for that oscillation. And this is then plotted to a new constructed volume amplitude signal at the appropriate time or applied pressure point along the waveform.

This procedure is then repeated for each and every oscillation in the transmural pressure function (FIG. 8) to thereby generate a complete waveform, representing peak-to-peak volume amplitude (y-axis) across the range of applied pressures $P_{app}$. The peak-to-peak amplitude signal may be represented as a function of cuff applied pressure, or as a function of a different variable such as time, depending upon the variable used in the transmural pressure function. The requirement is simply that the signal is a variation in the peak-to-peak amplitude of the arterial volume over that period when the applied pressure was varied by the blood pressure measurement cuff 32.

The above procedure for generating a signal representative of variation in peak-to-peak amplitude of arterial volume is performed for each generated sample (model) arterial volume function.

For each sample model $V_{art}$ function, the corresponding volume amplitude signal is compared with the volume amplitude signal (FIG. 10) derived from the true measurements.

The procedure is repeated iteratively (i.e. generation of a volume amplitude signal and comparison with the true volume amplitude signal) until a sufficiently closely matching volume amplitude signal is found.

The corresponding generated sample arterial volume function is then selected as the signal, $V_{a\text{-}osc}$, indicative of arterial volume as a function of arterial transmural pressure (for use in the subsequent steps for generating the output measure of arterial compliance).

In some examples, an initial or approximate measure of arterial compliance may be generated immediately at this point by differentiating the selected sample arterial volume function with respect to transmural pressure. This then results in a signal indicative of arterial compliance as a function of transmural pressure.

In addition to the above described procedure for deriving a signal representative of arterial volume variation as a function of transmural pressure, information indicative of pulse arrival time across the range of cuff applied pressures $P_{app}$ is also acquired. Hence pulse arrival time (PAT) is also measured while the cuff is gradually inflating (or deflating in alternative examples).

Pulse arrival time can be related to pulse wave velocity (PWV) which has a known relationship with compliance.

Pulse wave velocity, the rate at which pressure waves travel from the heart along an artery, is indicative of arterial stiffness, and therefore implicitly, arterial compliance.

However, PWV itself can be difficult to measure. Hence pulse arrival time (PAT) can instead be directly measured and then related back to PWV subsequently.

One example means for measuring the PAT is to determine the time difference (i.e. interval) between the R-peak of the ECG sensor device 22 signal R-wave, and some characteristic peak or other point in the PPG sensor 20 signal. This hence effectively gives a measure of the transit time of each blood pulse from the heart to the point at which the PPG sensor is attached (for example the subject's finger 40 (as illustrated in FIG. 3 for example)). After measuring the PAT, it is possible to directly derive the corresponding $$PWV = \frac{\text{Length}}{PAT - PEP} \tag{3}$$

where length refers to the distance (along the respective artery) travelled by the blood pulse between the heart and the point of measurement, and the PEP is the heart pre-ejection period. The pre-ejection period is a term of the art and means the period between occurrence of ventricular contraction (and opening of the semilunar valves) and commencement of blood ejection into the aorta.

As noted above, the PAT is measured as the cuff inflates, and thus as the applied pressure $P_{app}$ is varied across a range of increasing pressures. As the applied pressure increases, so the transmural pressure along the length of the cuff is altered, and this alters the PAT values.

As noted above, PWV embodies information indicative of elasticity characteristics of the artery. Relating measured PAT to PWV enables quantifying these elasticity characteristics. However, as PEP and length travelled by the pulse are difficult to measure, PAT can be related to PWV via a different relationship, set out in equation (4) below. This equation is based on the knowledge that the changes in PAT are primarily created at the region beneath the measurement cuff.

$$\Delta PAT(P_{tm}) = \left( \frac{1}{PWV(P_{tm})} - \frac{1}{PWV_{ref}} \right) \cdot L \tag{4}$$

Here, $PWV(P_{tm})$ is pulse wave velocity as a function of transmural pressure, $\Delta PAT$ is variation in pulse arrival time as a function of transmural pressure, and L is the length of a body-contacting portion of the oscillometry measurement device.

The PWV itself can be related to arterial compliance by means of the Bramwell-Hill equation below $$PWV(P_{tm}) = \sqrt{\frac{V(P_{tm})}{\rho C(P_{tm})}} \tag{5}$$

where $V(P_{tm})$ is arterial volume as function of transmural pressure, $C(P_{tm})$ is arterial compliance as function of transmural pressure, $\rho$ is blood density, and $PWV(P_{tm})$ is pulse wave velocity as a function of transmural pressure.

$PWV_{ref}$ is the pulse wave velocity at $P_{tm}$=MAP, where MAP is mean arterial pressure. Mean arterial pressure is the mean (or baseline) arterial pressure, $P_{art}$, within the artery when the cuff is not applying any external pressure. This can be derived from an arterial pressure signal $P_{art}$ (shown in FIG. 7) extracted from internal cuff pressure, $P_c$, in the process described above. It may be taken to be the baseline value of this signal for example. It may be taken as the baseline value of this signal when applied pressure is zero, i.e. at time t=0 in the example of FIG. 7 (and FIG. 5). Hence $PWV_{ref}$ may be given by $$PWV_{ref} = \sqrt{\frac{V(MAP)}{\rho C(MAP)}},$$

where the symbols C, $\rho$, and V have the same designations as outlined for equation (5) above.

Equations (4) and (5) above may be combined to provide a model of pulse arrival time which relates variation in pulse arrival time, $\Delta PAT$, arterial volume, $V(P_{tm})$, and arterial compliance $C(P_{tm})$:

$$\Delta PAT(P_{tm}) = \left( \frac{1}{\sqrt{\frac{V(P_{tm})}{\rho C(P_{tm})}}} - \frac{1}{PWV_{ref}} \right) \cdot L \tag{6}$$

According to one set of examples, a model-fitting procedure can be performed to fit to the model to an acquired (measured) pulse arrival time signal, and thus derive the $V(P_{tm})$ and $C(P_{tm})$ parameters which characterize the measured pulse arrival time signal. An example such procedure is described below.

According to one set of examples, in operation, while the blood pressure measurement cuff is gradually inflating, and thus the applied pressure to the artery 48 is gradually increasing through a range of pressures (see FIG. 5), the control unit 12 acquires using the ECG sensor device 22 and the PPG sensor 20 a signal indicative of a variation in pulse arrival time, $\Delta PAT$, at a particular location along said artery as said applied pressure is varied across said range of pressures. This will be referred to as $\Delta PAT_{meas}$.

Next (according to the present example), the control unit is adapted to iteratively generate different sample functions of arterial volume as a function of transmural pressure and of arterial compliance as a function of transmural pressure.

This can be done using equation (2) above, by sampling different sets of parameters a, c and d. This results in different sample $V_{art}(P_{tm})$ functions. Each of these can be differentiated with respect to transmural pressure $P_{tm}$ to result in a corresponding function of arterial compliance as a function of transmural pressure, $C(P_{tm})$.

For each sample arterial volume function and corresponding arterial compliance function pair, a corresponding modeled function of pulse arrival time, $\Delta PAT(P_{tm})$, is generated using the pulse arrival time model equation (6) above, i.e. by substituting in the sample $V(P_{tm})$ and $C(P_{tm})$ functions into equation (6) (along with the other parameters).

Each resulting sample modeled function of pulse arrival time is then compared with the above acquired signal indicative of variation in pulse arrival time, $\Delta PAT_{true}$. Hence the sampled function is compared with the true measured pulse arrival time variation signal.

The sampling of different trial $V(P_{tm})$ and corresponding $C(P_{tm})$ functions may be iteratively continued until a sufficiently closely fitting $\Delta PAT(P_{tm})$ function is found.

The above-described model-fitting procedure may be performed using the same Markov chain Monte Carlo (MCMC) sampling approach discussed above. Again, implementation of such a fitting procedure will be well known to the skilled person and will not be outlined in detail in this disclosure.

In summary, the above model fitting procedure comprises iteratively sampling a series of different sets of parameters for the above arterial volume model (2), then for each set, the resulting sample $V_{art}$ model function is differentiated to derive a corresponding compliance function. The $V_{art}$ and Compliance function are used to generate a corresponding sample $\Delta PAT(P_{tm})$ function (equation (6)). This is compared with the true $\Delta PAT_{true}$ function, and based on the comparison result, new functions may be iteratively re-sampled until a sufficiently closely matching $\Delta PAT(P_{tm})$ function is found.

At the end of this procedure, the corresponding $V(P_{tm})$ and $C(P_{tm})$ functions may then be directly obtained. Hence compliance information is obtained.

Combination of the PAT-derived compliance information and the above oscillometry derived compliance information (based on volume variations) may be achieved in different ways.

According to one set of examples, the final derived signal, $V_{a\text{-}osc}$, indicative of arterial volume as a function of arterial transmural pressure, derived from the oscillometric blood pressure measurements, may be first differentiated (if this has not been done already) with respect to transmural pressure to derive a corresponding signal indicative of arterial compliance.

This oscillometric arterial volume signal, $V_{a\text{-}osc}$, and corresponding compliance signal may then be substituted into the pulse arrival time model signal (5) above to generate a corresponding modeled pulse arrival time function for the $V_{a\text{-}osc}$ signal and corresponding compliance signal.

This generated model pulse arrival time function may be used as prior information in the model fitting procedure referred to above for identifying the $\Delta PAT(P_{tm})$ function for the measured PAT signal. For example, each generated sample $\Delta PAT(P_{tm})$ function derived from sample generated $V(P_{tm})$ and $C(P_{tm})$ functions may be compared both with the true measured $\Delta PAT_{true}$ signal and also with the generated model $\Delta PAT(P_{tm})$ function generated form the oscillometric information. Similarity with respect to each may be taken into account in selecting the final sample $\Delta PAT(P_{tm})$ function. Minimum similarity thresholds, or constraints with respect to both may be imposed for instance.

Thus the final sample generated $\Delta PAT(P_{tm})$ function would satisfy a minimum level of similarity with respect to both the oscillometric-derived information and the measured $\Delta PAT_{true}$ information.

Hence both input sources of information combine to generate the final modeled $\Delta PAT(P_{tm})$ function.

From this can be directly obtained the corresponding arterial compliance function $C(P_{tm})$ function parameter (see equation (6) above). This compliance function provides an output measure of arterial compliance.

The control unit 12 may for example generate an output data signal representative of this final measure of arterial compliance.

The PAT-derived compliance information and the oscillometry derived compliance information (based on volume variations) can be combined in other ways.

For example, rather than deriving the final modeled $\Delta PAT(P_{tm})$ using the oscillometric compliance information as prior information with which the PAT information is compared, independent compliance measures may be generated (for instance simultaneously) using each of the oscillometry information and the PAT information respectively. These measures may then be combined, for example by an averaging procedure, or any other combination procedure.

One measure might be weighted more heavily than the other in this combination, for instance based on an estimated relative degree of noise in the signals used to derive each of the measures.

In other examples, the PAT information may be used as prior information for informing derivation of compliance from the oscillometry measurements, instead of the oscillometric compliance information being used as the prior.

In further examples, neither the PAT information nor the oscillometry information may be used as prior. Instead, at each iteration, a single simulated compliance value (or arterial volume measure) may be compared to both PAT-derived information (e.g. PAT derived compliance) and the oscillometric information (e.g. oscillometric-derived compliance).

A loss function may be used to account for disparity or differences with respect to the two sets of information. This for instance allows the possibility of using a different measure or source of information as prior for the model fitting, for instance another clinical parameter, or another pre-determined relationship between certain parameters.

When implementing the system, it typically may undergo an initial trial period within a specific clinical setting. Clinical trials can reveal differences which may manifest in the final derived compliance measures, and also between the oscillometric derived and PAT derived compliance measures, in different clinical scenarios. In ideal cases, clinical trials take place using a hospital's own measurement devices (e.g. using a certain choice of blood pressure cuff). Depending upon the available measurement devices, a certain degree of accuracy in the compliance measurement may be achieved. This accuracy may be determined for example based on a known sample rate of the specific measurement system, a standard error in the PPG signal, the duration of the cuff inflation (number of heart beats recorded in the measurement), any effects of breathing artefacts and any other relevant factors which may affect measurements in the actual clinical scenario.

Assessment of these factors may inform selection of appropriate weights for the oscillometric and PAT information within the compliance measure derivation process for example.

The model-fitting procedure described above comprises selecting as the final modeled $\Delta PAT(P_{tm})$ function (and thus also the final corresponding estimated compliance value) that model with the highest comparison or similarity score with the measured PAT function and/or the oscillometry-based modeled $\Delta PAT$ function.

In further examples, a distribution of possible compliance measurement values may be taken into account, having less than maximum similarity to measured data or measured PAT functions. For instance, the whole set of trialed model functions (e.g. PAT functions) may in some examples be considered, along with their relative similarity scores, and from this may be determined a measure of uncertainty in the final derived compliance measure value. For example, a spread or variance in the possible compliance values, taking into account their relative probabilities of accuracy, may be considered, and a measure of uncertainty derived from this.

This approach is part of standard Bayesian techniques and will be well known the skilled person. For this reason, it will not be outlined in detail here. The skilled person will be aware of how to implement such approaches.

The derived measure of uncertainty may for example be displayed on a display panel of the system, for instance on a display panel of a patient monitor device.

The quantification of uncertainty may in some examples be used to automatically trigger additional measurements, or may simply be used in aiding a clinician in deciding upon further investigations, such as more invasive types of monitoring.

Examples in accordance with a further aspect of the invention provide a system (10) for deriving a measure of arterial compliance, comprising a control unit (12) in accordance with any of the examples or embodiments described above or in accordance with any claim of this application: an oscillometric blood pressure measurement device operatively coupled to the control unit; and means for measuring a pulse arrival time, operatively coupled to the control unit.

According to one or more examples, the system may further comprise a patient monitor unit. The patient monitor unit may comprise the control unit for example.

As discussed above, embodiments make use of a control unit. The control unit may be a controller. The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A controller for deriving a measure of arterial compliance, operably couplable in use with an oscillometric blood pressure measurement device,
the controller adapted to:
receive, from the oscillometric blood pressure measurement device, an arterial volume signal indicative of a variation in arterial volume of an artery assumed to be in contact with the measurement device, as a pressure applied to the artery by the measurement device is varied across a range of pressures;
extract from said arterial volume signal a peak-to-peak volume amplitude signal indicative of a peak-to-peak amplitude of the arterial volume across said range of applied pressures;
receive a signal indicative of a variation in pulse arrival time at a particular location along said artery as said applied pressure is varied across said range of pressures;
derive from said extracted peak-to-peak volume amplitude signal, a signal, $V_{a\text{-}osc}$, indicative of arterial volume as a function of arterial transmural pressure, based on a first model fitting procedure employing a pre-determined arterial volume model; and
derive an output measure indicative of arterial compliance based on the derived $V_{a\text{-}osc}$ signal and based on the acquired signal indicative of variation in pulse arrival time, using a further model fitting procedure employing a pre-determined pulse arrival time model relating variation in pulse arrival time, arterial volume, and arterial compliance.

2. The controller as claimed in claim 1, wherein the pulse arrival time model is based on a relationship between pulse arrival time and pulse wave velocity, and a relationship between pulse wave velocity, arterial volume and arterial compliance.

3. The controller as claimed in claim 1, wherein the $V_{a\text{-}osc}$ signal is used to inform fitting of the pulse arrival time model.

4. The controller as claimed in claim 1, wherein the further model fitting procedure comprises:
iteratively generating different sample functions of arterial volume as a function of transmural pressure and of arterial compliance as a function of arterial pressure;
generating, using the pulse arrival time model, a corresponding modeled function of pulse arrival time for each sample arterial volume function, and
in each case comparing the resulting modeled function of pulse arrival time with the acquired signal indicative of variation in pulse arrival time.

5. The controller as claimed in claim 4, wherein the different sample functions of arterial compliance are generated by taking the derivative of each sample function of arterial volume with respect to arterial transmural pressure.

6. The controller as claimed in claim 4, wherein the further model fitting procedure comprises:
deriving a signal indicative of arterial compliance by differentiating the derived $V_{a\text{-}osc}$ signal with respect to transmural pressure;
generating a modeled pulse arrival time function, $\Delta PAT_{osc}$, by substituting the derived $V_{a\text{-}osc}$ signal and the derived signal indicative of arterial compliance into the pulse arrival time model; and
comparing each of the generated modeled pulse arrival time functions of claim 4 with the modeled pulse arrival time function $\Delta PAT_{osc}$.

7. The controller as claimed in claim 1, wherein the pulse arrival time model has the form:

$$\Delta PAT(P_{tm}) = \left(\frac{1}{PWV(P_{tm})} - \frac{1}{PWV_{ref}}\right) \cdot L$$

where $$PWV(P_{tm}) = \sqrt{\frac{V(P_{tm})}{\rho C(P_{tm})}}$$

where PWV($P_{tm}$) is pulse wave velocity as a function of transmural pressure, $\Delta$PAT is variation in pulse arrival time, V($P_{tm}$) is arterial volume as function of transmural pressure, C($P_{tm}$) is arterial compliance as function of transmural pressure, $\rho$ is blood density, L is the length of a body-contacting portion of the oscillometry measurement device, and $PWV_{ref}$ is the pulse wave velocity at $P_{tm}$=MAP, where MAP is mean arterial pressure.

8. The controller as claimed in claim 1, wherein the controller is further operably couplable in use with an ECG sensor device and a PPG sensor.

9. The controller as claimed in claim 1, wherein the acquiring the signal indicative of arterial volume variation comprises:
controlling an inflatable cuff of the oscillometric measurement device to gradually inflate to thereby vary said applied pressure to the artery beneath the cuff through said range of applied pressures.

10. The controller as claimed in claim 1, wherein the first model fitting procedure comprises:
generating different sample functions of arterial volume as a function of transmural pressure using the arterial volume model;
extracting from each sample function a corresponding sample signal representative of variation in peak-to-peak amplitude of arterial volume across said range of applied pressures; and
comparing each sample peak-to-peak volume amplitude signal with the extracted volume amplitude signal of claim 1.

11. The controller as claimed in claim 1, wherein the pre-determined arterial volume model is based on a relation having the form $$V(P_{tm}) = d \cdot L \cdot \frac{\ln(a * P_{tm} + 3.3)}{\left(1 + e^{-c*P_{tm}}\right)}$$

where V($P_{tm}$) is arterial volume as a function of arterial transmural pressure, a, c and d are fitting parameters for the model, $P_{tm}$ is transmural pressure and L is a length of a body-contacting portion of the oscillometric measurement device.

12. A system for deriving a measure of arterial compliance, comprising:
the controller as claimed in claim 1;
an oscillometric blood pressure measurement device operatively coupled to the controller; and
an ECG sensor device and a PPG sensor, operatively coupled to the controller.

13. The system according to claim 12, further comprising a patient monitor, the patient monitor comprising the controller.

14. A method of deriving a measure of arterial compliance, comprising:
receiving, from an oscillometric blood pressure measurement device, an arterial volume signal indicative of variation in arterial volume of an artery assumed to be in contact with the measurement device, as an applied pressure to the artery by the oscillometric measurement device is varied across a range of pressures;
extracting from said arterial volume signal a peak-to-peak volume amplitude signal indicative of a variation in peak-to-peak amplitude of arterial volume across said range of applied pressures;
receiving a signal indicative of a variation in pulse arrival time at a particular location along said artery as said arterial transmural pressure is varied across said range of pressures;
deriving from said extracted peak-to-peak volume amplitude signal, a signal, $V_{a-osc}$, indicative of arterial volume as a function of arterial transmural pressure, based on a model fitting procedure employing a pre-determined arterial volume model; and
deriving an output measure indicative of arterial compliance based on the derived $V_{a-osc}$ signal and based on the acquired signal indicative of variation in pulse arrival time, the deriving being based on a further model fitting procedure employing a pre-determined pulse arrival time model relating variation in pulse arrival time, arterial volume, and arterial compliance.

15. The method as claimed in claim 14, further comprising a preliminary step of fitting the oscillometric measurement device to a part of a subject's body, with the device positioned above an artery for applying a variable pressure to said artery.

* * * * *